Figure 1:
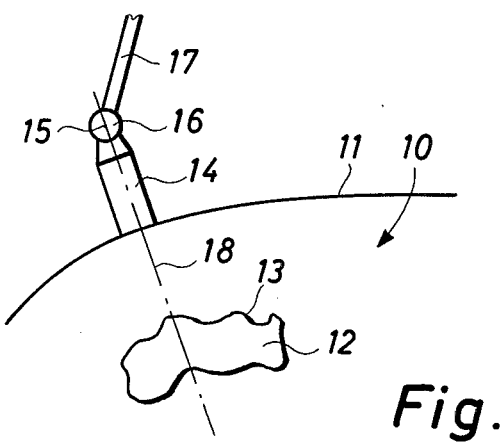

4,030,344

United States Patent [19]
Northeved et al.

[11] 4,030,344
[45] June 21, 1977

[54] APPARATUS FOR RECORDING AN ULTRASONIC SECTIONAL VIEW

[75] Inventors: Allan Northeved, Bagsvaerd; Knud Christian Claus Fabrin, Farum; Poul Solfjeld, Horsholm, all of Denmark

[73] Assignee: Akademiet for de tekniske Videnskaber, Svejsecentralen, Denmark

[22] Filed: May 7, 1976

[21] Appl. No.: 684,437

[30] Foreign Application Priority Data
May 12, 1975 Denmark .............................. 2084/75

[52] U.S. Cl. ...................... 73/67.8 S; 73/71.5 US; 128/2 V
[51] Int. Cl.² .......................................... G01N 9/24
[58] Field of Search ................. 73/67.8 S, 71.5 US; 128/2 V, 2.05 Z

[56] References Cited
UNITED STATES PATENTS

| | | | |
|---|---|---|---|
| 3,086,390 | 4/1963 | Brown | 128/2 V |
| 3,541,840 | 11/1970 | Phelan | 73/71.5 US |
| 3,555,888 | 1/1971 | Brown | 73/71.5 US |
| 3,714,817 | 2/1973 | Miller | 73/71.5 US |
| 3,864,660 | 2/1975 | Ranalli et al. | 128/2 V |

*Primary Examiner*—James J. Gill
*Assistant Examiner*—Anthony V. Ciarlante
*Attorney, Agent, or Firm*—Ladas, Parry, Von Gehr, Goldsmith & Deschamps

[57] ABSTRACT

An apparatus for providing an ultrasonic sectional view of a body to be examined. The apparatus comprises a transducer head in the form of a wheel in the periphery of which four ultrasonic transducers are built in. The wheel rotates about an axis perpendicular to the sectional plane. The apparatus further comprises means for separately and successively cutting the transducers in and out of a pulse circuit in such a manner that each transducer covers only a sector from −45° to +45° with regard to a symmetry axis for the transducer head.

4 Claims, 10 Drawing Figures

APPARATUS FOR RECORDING AN ULTRASONIC SECTIONAL VIEW

The present invention relates to an apparatus for recording an ultrasonic sectional view comprising a transducer head with a pulse circuit for transmission and reception of ultrasonic energy, means for visualizing received reflected ultrasonic signals on a cathode-ray tube, and a scanning arm for moving the transducer head in a sectional plane along a plane curve corresponding to the outline of the body examined in the sectional plane, said apparatus comprising data potentiometers and analogous calculating circuits for producing electrical signals representing the positions of the reflection points of the ultrasonic echoes in a rectangular XY-system of coordinates in the sectional plane.

The known methods for recording ultrasonic sectional views disclose an ultrasonic head comprising a single ultrasonic transducer and being pivotally mounted at the end of a scanning arm. The ultrasonic energy is transmitted into the body to be examined in the form of a narrow beam with a small opening angle. Only the reflected energy following the longitudinal axis of the ultrasonic head can be detected by the ultrasonic head and registrated or visualized on an oscilloscope screen. It is obvious that only the tissue interfaces perpendicular to the symmetry axis of the ultrasonic head and of the ultrasonic energy transmitted cause ultrasonic echoes detectable by the ultrasonic head and which may be visualized on the oscilloscope screen. In order to provide a satisfactory ultrasonic sectional view by means of such equipment the operator has hitherto been reduced in each position of the scanning arm to turn or tilt the ultrasonic head manually in the sectional plane in order to make the symmetry axis of the ultrasonic head gradually cover a circular sector in the sectional plane with a suitably great opening angle. This procedure is repeated in the next scanning position. By such a method it is rather time-consuming to produce a single ultrasonic sectional view of a large organ sector containing a satisfactory quantity of information. Apart from the fact that it is time-consuming, it is very tiring for the operator that he must constantly handle the ultrasonic head in the above way. As far as the patients are concerned such a long examination may as well be rather inconvenient.

The object of the invention is to provide an apparatus of the type stated in the opening paragraph which removes the above drawbacks.

An essential feature of the apparatus according to the invention is that the transducer head comprises four ultrasonic transducers built into the periphery of a transducer wheel at equidistant angular distance for bound rotation about an axis perpendicular to the sectional plane, said transducer wheel comprising means for separately and successively cutting the transducers in and out of the pulse circuit in such a manner that each transducer covers only a sector (angle D) from $-45°$ to $45°$ about a symmetry axis for the transducer head, the transducer head comprising a sine-cosine potentiometer mechanically coupled to the transducer wheel for the registration of the angle, and that the apparatus comprises means for resetting the angle 90°, said angle being registrated by the sine-cosine potentiometer at each changing over from one transducer to the subsequent one.

The apparatus according to the invention may have the peculiar feature that an asynchronous motor with an infinitely variable gear indirectly drives the transducer wheel through a Bowden cable and a chain drive. By establishing a chain drive between the transducer wheel and the Bowden cable it is rendered possible to introduce the Bowden cable into the transducer in a manner substantially coaxial with the axis, about which the transducer head rotates at the end of the scanning arm. This embodiment has the advantage that the tilting of the transducer head about this axis is not considerably hampered by the Bowden cable.

The infinitely variable gear permits recording of both dynamic and static scanning views.

By quick rotation of the transducer wheel a real time scanning view of a sector in the sectional plane may be obtained, i.e. the sector covered by each transducer during the rotation of the wheel. A series of dynamic sectors are produced if the transducer head is simultaneously moved across the patient, and in this manner a gradually real time view of the sectional plane is obtained.

By slow rotation of the transducer wheel a static and complete ultrasonic view of the sector examined in the sectional plane may within a period of about 5 sec. be obtained by one movement only of the transducer head. This ultrasonic view is made up of a series of static sector views. Thus it is rendered possible to produce a static view of the sectional plane containing sufficient information in a very short time.

Moreover according to the invention the means for separately and successively cutting the transducers in and out of the pulse circuit may comprise four reed switches built into the transducer wheel, one side of said reed switches being connected to a transducer and the opposite side being connected in parallel via a slip ring on the axis of the ransducer wheel to a common conductor secured to said axis of the transducer wheel, on which slip ring a slip contact is slipping, said slip contact being connected to the pulse circuit by means of the inner conductor of a coaxial cable; and a fixed permanent magnet for activating the reed switches separately and a relay contact inserted in the pulse circuit and controlled by a control circuit, said relay contact only connecting the individual transducer to the pulse circuit when the associated reed switches have been opened and closed respectively.

The inventive means for a 90° resetting of the angle registrated by the sine-cosine potentiometer at each changing over from one transducer to the subsequent one may furthermore comprise a plurality of operational amplifiers providing the functions sineD, cosineD, $-$sineD, $-$cosineD, a plurality of comparators coupled to their respective operational amplifiers and to a reference DC source, and wherein the outputs of the comparators control a plurality of analogous gates in order to provide a sine voltage on a sine output varying from $-\sqrt{2/2}$ to $\sqrt{2/2}$ and a cosine voltage on a cosine output varying from $-\sqrt{2/2}$ to 1 and back to $-\sqrt{2/2}$ from the moment when a transducer is cut in and till the moment when said transducer is cut out.

Figure 5:
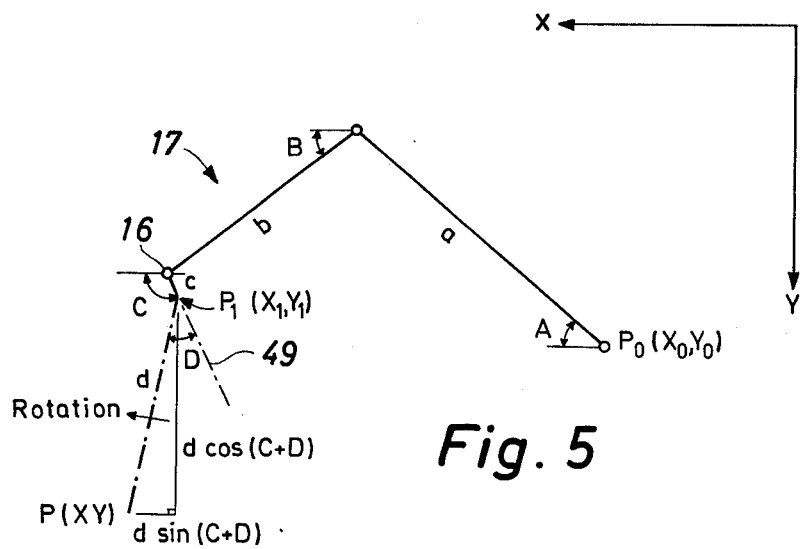
Figure 4:
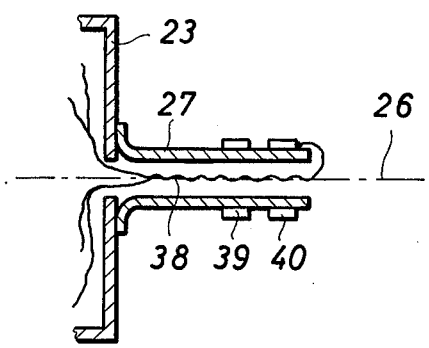
Figure 3:
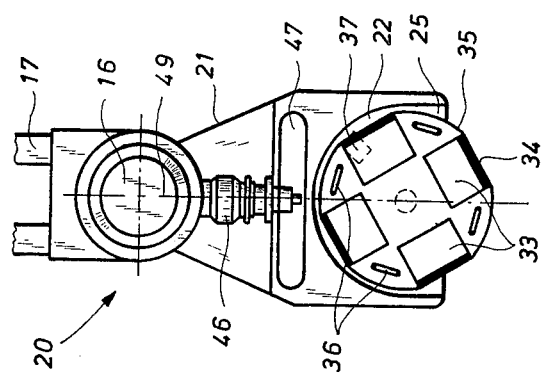
Figure 2:
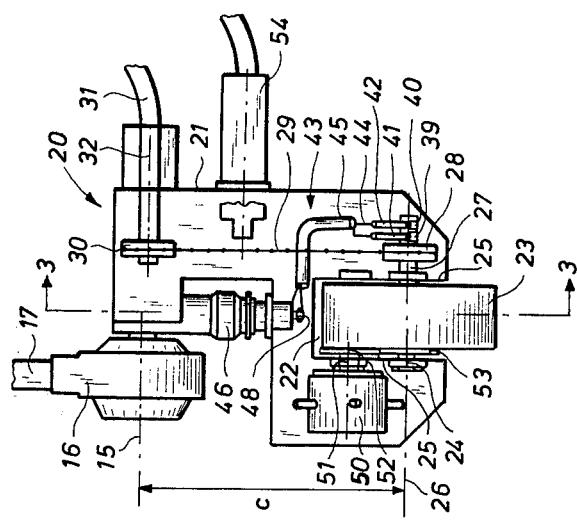
Figure 6:
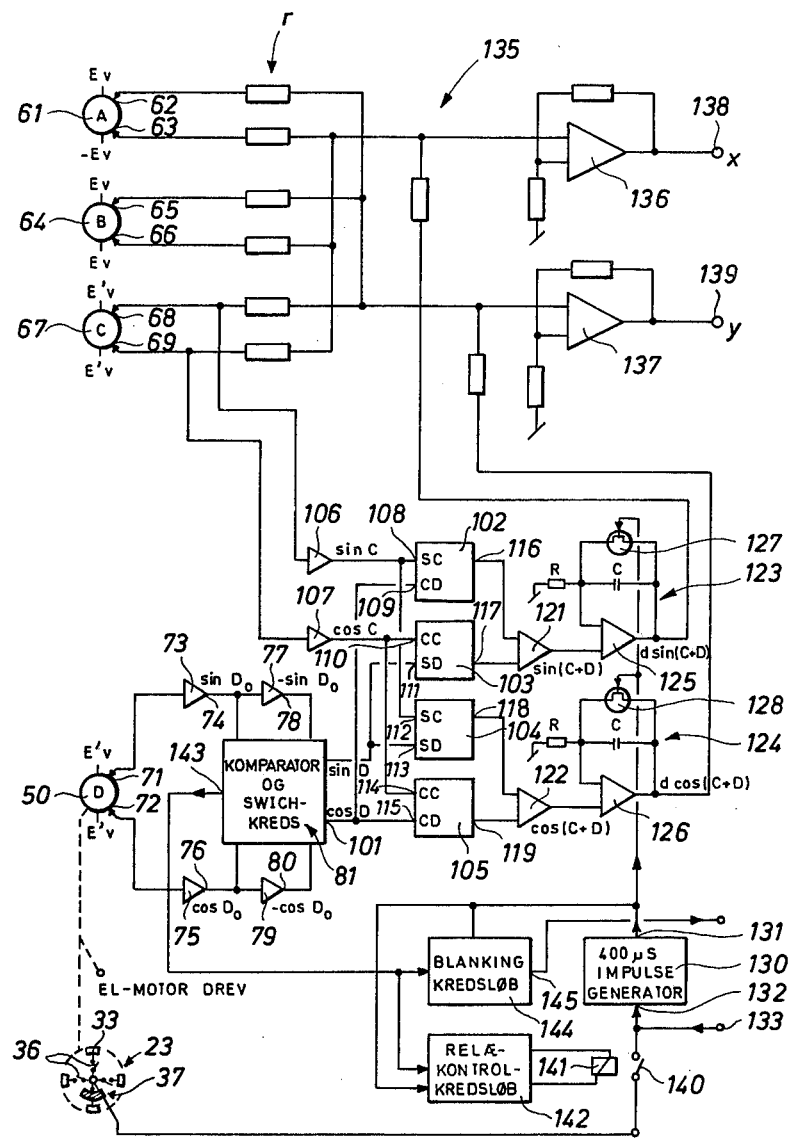
Figure 7:
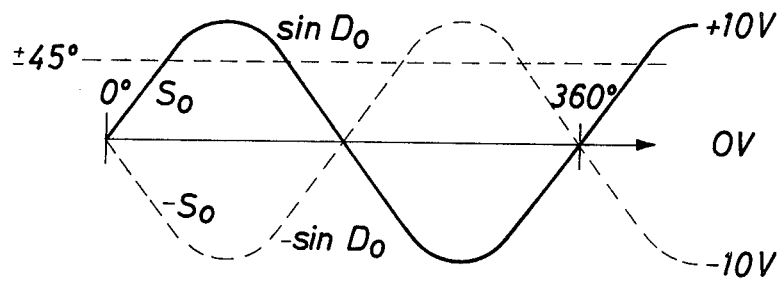
Figure 8:
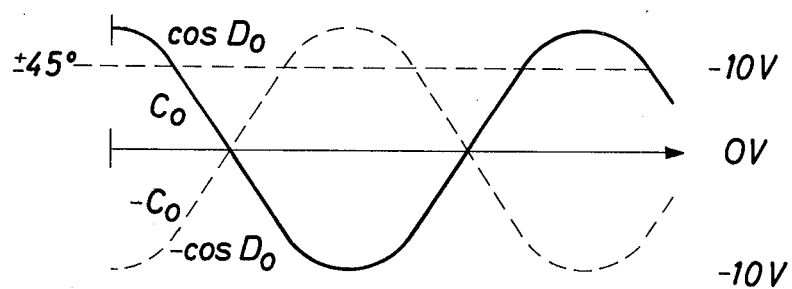
Figure 9:
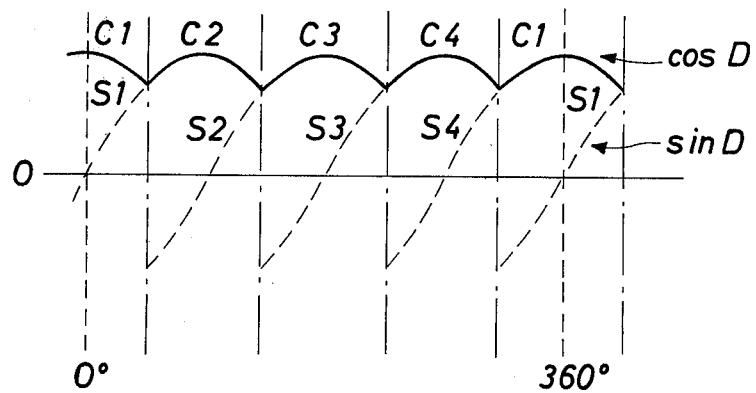
Figure 10:
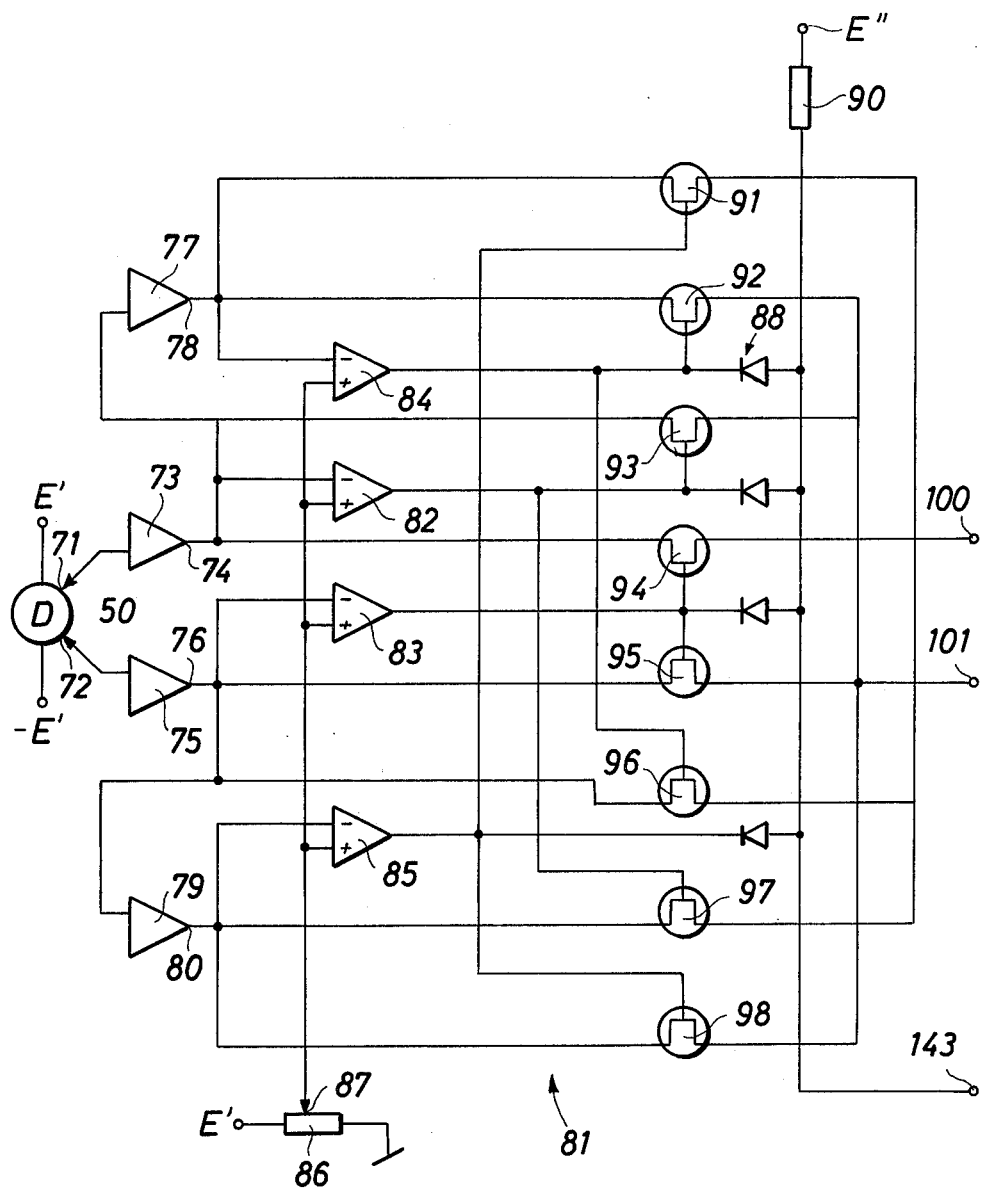

The invention will be described below with reference to the accompanying drawings, in which FIG. 1 is a very diagrammatic view of the hitherto used apparatus for producing an ultrasonic sectional view in a sectional plane of a human body, FIG. 2 is a longitudinal sectional view of an ultrasonic head according to the invention, FIG. 3 is a sectional view taken along the line 3—3 of FIG. 2, FIG. 4 is a sectional view of the transducer wheel according to the invention, FIG. 5 illustrates the geometry in the sectional plane at the split scanning arm, FIG. 6 is a block diagram of an electric circuit providing an electric representation of the coordinates in the sectional plane of a reflection point P in the interior of a patient, FIGS. 7 and 8 illustrate the output voltages of a sine-cosine potentiometer driven by the transducer wheel and inverted values of these voltages, FIG. 9 shows the desired operation of the function sineD and cosineD during the rotation of the transducer wheel, and FIG. 10 illustrates a detailed block diagram of the comparator- and switch circuits of FIG. 6.

FIG. 1 illustrates a sectional plane of a portion of a human body 10 with an outline 11 and an internal organ 12. The outline of the organ 12 is indicated by a closed curve 13 in the sectional plane. The indicated sectional view may for instance be through abdomen. By conventional methods for recording ultrasonic sectional views an ultrasonic head 14 is used. The head 14 is pivotally mounted about a tilt axis 15 by means of a swivel 16 at the end of a scanning arm 17. The ultrasonic energy is transmitted in the body 10 in the form of a narrow beam with a small opening angle with a symmetry axis or a main axis 18. Only the energy reflected following this axis is detected or visualized in a known manner, e.g. on an oscilloscope screen. It is obvious that only the tissue interfaces perpendicular to the symmetry axis of the ultrasonic head and of the ultrasonic energy transmitted cause ultrasonic echoes detectable by the ultrasonic head and which may be visualized on the oscilloscope screen. In order to provide a satisfactory ultrasonic sectional view by means of such equipment the operator has hitherto been reduced in each position of the scanning arm to turn or tilt the ultrasonic head manually in the sectional plane in order to make the symmetry axis of the ultrasonic head gradually cover a circular sector in the sectional plane with a suitably great opening angle. This procedure is repeated in the next scanning position. By such a method it is rather time-consuming to produce a single ultrasonic sectional view of a large organ sector containing a satisfactory quantity of information. Apart from the fact that it is time-consuming, it is very tiring for the operator that he must constantly handle the ultrasonic head in the above manner. As far as the patients are concerned such a long examination may be as well be rather inconvenient.

In order to overcome these drawbacks the previous ultrasonic head 14 comprising only one ultrasonic transducer has been replaced by another ultrasonic head comprising a wheel rotatable about another axis parallel to the tilt axis 15 and furthermore provided with four equal transducers. The inventive head shown generally at 20 appears in detail from FIGS. 2 and 3.

The ultrasonic head 20 comprises a housing 21 mounted pivotally about the tilt axis 15 at the end of the scanning arm 17. The housing 21 is at its free end provided with a recess 22 for the transducer wheel 23. The transducer wheel 23 is mounted in bearings 24 in the side walls 25 of the recess 22 rotatable about an axis 26 parallel to the tilt axis 15. Thus the wheel is partly encapsulated and consequently well protected.

One side of the shaft 27 of the transducer wheel is extended and projects somewhat into the housing 21. The shaft 27 is a fixed shaft, i.e. it rotates together with the wheel. A first chain wheel 28 is mounted on the shaft 27 in the housing 21. Furthermore the shaft 27 is hollow due to circumstances described in the following. The chain wheel 28 is connected via a ball chain 29 to another chain wheel 30 mounted at the end of the Bowden cable 31. The Bowden cable 31 is led through the housing 21. Thus the axis of rotation 32 of the second chain wheel 30 is substantially identical with the tilt axis 15 of the transducer head. The Bowden cable is driven by an asynchronous motor with an infinitely variable gear (not shown in detail) whereby the transducer wheel 23 may rotate either slowly, i.e. with a speed of rotation of 10 r/m or fast, i.e. with a speed of rotation of 100 r/m. The advantage of this embodiment has already been mentioned in the introduction.

The Bowden cable may, of course, drive the transducer wheel directly, but the indirect drive through the chain drive 28, 29, and 30 provides a large freedom of movement during the tilting of the transducer head due to the fact that the Bowden cable will not hamper this movement.

The transducer wheel 23 is provided with four 2 MHz ultrasonic transducers 33, cf. the illustrated embodiment. The transducers are built radially into the wheel 23 at 90° intervals with their fronts 34 at the periphery of the wheel. Only one at a time of the four transducers is electrically coupled to the ultrasonic apparatus during the scanning procedure, i.e. the uncovered transducer being in contact with the body surface of the patient. The separate and successive cutting-in and out of the four transducers during the rotation of the wheel 23 is performed by means of four reed switches 36 embedded in the wheel 23 and by means of a fixed adjustable permanent magnet 37. The reed switches 36 are closed when subjected to the magnetic field of the permanent magnet 37 and open when not subjected to this magnetic field. The permanent magnet 37 is dimensioned, disposed, and protected in such a manner that only one reed switch at a time is activated. Thus only the transducer being in contact with the patient transmits and receives ultrasonic energy.

The electrical connection between transducers, reed switches and the external equipment is established through the hollow portion of the shaft 27. One side of the four reed switches 36 is connected to a transducer 33, the shield of which is electrically connected in a known manner to the transducer wheel. Thus the wheel forms part of the electric shield and serves as a common frame connection. The other side of the four reed switches 36 is connected to a common insulated conductor 38 led through the hollow shaft 27, cf. FIG. 4.

FIG. 4 illustrates the side of the transducer wheel 23 supporting the hollow shaft 27. A first and a second slip ring 39 and 40 are disposed at the end of the shaft. The first slip ring 39 is in direct electrical connection with the shaft whereas the second slip ring 40 is electrically insulated relative to the shaft. The common insulated conductor 38 of the reed switches is led through the shaft and electrically connected to the other slip ring 39, e.g. by soldering. The slip rings are made of a wear-resisting well conducting material, e.g. gold.

The electrical connection is provided by means of a first and a second slip contact 41 and 42 respectively. Said contacts are connected to a coaxial cable 43 with an inner conductor 44 and a shield 45 connected to a TNC plug. The TNC plug is connected to a signal pulse conductor 60, cf. FIG. 6. The first contact 41 slips on the first slip ring 39 and is connected to the shield 45 of the coaxial cable. The shield 45 is connected to the external portion of the TNC plug 43 being electrically connected to the housing 21. A recess 47 is provided in the housing 21, cf. FIG. 3, permitting the installation of the TNC plug. The recess has furthermore been made as large as possible with a view to the weight.

Thus the shields of the ultrasonic transducers have effectively been brought at a common zero potential via the transducer wheel 23, the shaft 27, the first slip ring 39, the first slip contact 41, the shield 45 of the coaxial cable, and the external portion of the TNC plug being the connection to the housing 21.

The second slip contact 42 slips on the second slip ring and is connected to the inner conductor 44 of the coaxial cable. The inner conductor 44 is connected to an inner conductor 48 in the TNC plug. In this manner the pulse-forming curcuit from the pulse conductor 50 to the transducers is established via the inner conductor 48 of the TNC plug, the inner conductor 44 of the coaxial cable, the second slip contact 42, the second slip ring 40, the common conductor 38 of the transducers, and finally the reed switch being closed at the moment in question, cf. also the bottom left-hand corner of FIG. 6.

The position of the activated transducer is transferred to the electronic unit of the scanner via a sine-cosine potentiometer 50 mounted in the interior of the housing 21 of the transducer head. The potentiometer 50 is mounted in a bearing 51 on the side wall 25 in the recess 22 removed from the chain drive 28, 29, and 30.

A set of gear wheels are disposed in the recess 22 in the gap between the above side wall 25 and the transducer wheel. One of said gear wheels 52 is mounted on the shaft of the potentiometer 50, and the other gear wheel 53 is mounted on the shaft of the transducer wheel. The position of the transducer wheel is transferred by means of these two gear wheels 52 and 53 to the sine-cosine potentiometer. In this manner the sine output and the cosine output of the potentiometer pass through all the function values of an angle passing through the interval from 0° to 360° one time per revolution.

The reference voltages to and the signal voltages from the potentiometer are provided via a plug 54 of the plug-in type. The supply lines of this plug to the potentiometer have not been illustrated since the illustration would complicate the drawing unnecessarily, and furthermore since it must be regarded as being obvious to a person skilled in the art to establish such connections.

As mentioned in connection with FIG. 1 the transducer head is driven by means of a scanning arm 17 during the scanning procedure. The transducer head 20 may, of course, by manually driven in the sectional plane, but in most cases it has proved to be most advantageous to dispose the transducer head at the end of the scanning arm. FIG. 5 shows the above scanning arm. The arm is split and of a common type used in several hospitals. The mechanical structure of the arm will therefore not be described, and only the geometry in the sectional plane of the arm is illustrated.

The point P in the Figure illustrates a point in the interior of a patient, and this point causes an ultrasonic echo that is to be visualized on an oscilloscope screen with the correct disposal in relation to other repeated ultrasonic echoes. The point P has the coordinates $(x, y)$ in a rectangular XY-system of coordinates in the sectional plane.

A point $P_0$ with the coordinates $(X_0, Y_0)$ designates a reference point in the sectional plane and is placed in the suspension point of the scanning arm 17. In this suspension point the first link of the arm with a bar length $a$ is mounted in a swivel comprising a first sine-cosine potentiometer for registration of the angle A between a horizontal plane and the first link of the arm. The second link of the arm with a bar length $b$ is mounted at the end of the first link at a swivel comprising a second sine-cosine potentiometer for registration of the angle B between a horizontal plane and the second link of the arm. The transducer head is mounted on a third swivel disposed at the end of the second link of the arm. The third swivel is indicated by 16 in FIG. 2, and comprises a third sine-cosine potentiometer for registration of the angle C between a horizontal plane and the symmetry axis of the transducer indicated by 49 in FIG. 3. The distance between the axis 15 about which the transducer head rotates and the axis about which the transducer wheel 23 rotates is constantly referred to as c. The intersection of the axis of rotation 26 with the sectional plane is indicated by $P_1$ and allocated the coordinates $(x_1, y_1)$ as expressed by the bar lengths $a$, $b$, and $c$ and the angles A, B, and C:

$$x_1 = x_0 + a\text{cosine}A + b\text{cosine}B + c\text{cosine}C \tag{I}$$

$$y_1 = y_0 + a\text{sine}A + b\text{sine}B + c\text{sine}C \tag{II}$$

The constants $a$, $b$, and $c$ may be represented by means of the reference voltages, and the trigonometric functions may be reprsented by means of the above three sine-cosine potentiometers. The reference position $P_0$ $(X_0, Y_0)$ is represented by means of reference DC voltages applied to the deflection plates of the oscilloscope in a known manner.

A fourth sine-cosine potentiometer registrates the rotation of the transducer wheel 23, and is indicated by 50 in FIG. 2. An angle D is measured between the symmetry axis 49 of the transducer head and the main axis 18 of the activated transducer 34, cf. of FIG. 1.

Since the transducer wheel 23 is driven by force by an asynchronous motor, and since the individual transducer is cut in and out one time per revolution, it is not possible to move the angle D to a horizontal plane in a simple manner on equal term with the other angles A, B, and C. If the distance between the reflection point P in the interior of the patient and the axis of rotation of the wheel is designated $d$ the following coordinates $(x, y)$ in the sectional plane for the point P are obtained:

$$x = x_1 + d\text{sine}(C + D) \tag{III}$$

$$y = y_1 + d\text{cosine}(C + D) \tag{VI}$$

Since the functions of the angle C + D are not directly available it is necessary to utilize the summary formulae of sine and cosine and the equations are rewritten into:

$$x = x_1 + d(\text{sine}C\ \text{cosine}D + \text{cosine}C\ \text{sine}D) \tag{V}$$

$$y = y_1 + d(\text{cosine}C\ \text{cosine}D - \text{sine}C\ \text{sine}D) \tag{VI}$$

The circuit shown in FIG. 6 is used for providing these $x$ and $y$-values. The above first sine-cosine potentiometer registrating the angle A is indicated by 61. The reference DC voltages ± E volt are applied to the fixed terminals of the sine-cosine potentiometer, whereby a DC voltage proportional to sineA appears on the sine output 62 of the first sine-cosine potentiometer, and a DC voltage proportional to cosineA appears on the cosine output 63 of said potentiometer.

The second sine-cosine potentiometer registrating the angle B is indicated by 64. The reference DC voltages ± E volt are applied to the fixed terminals of the second sine-cosine potentiometer, whereby a DC voltage proportional to sineB appears on the sine output 65 of the second sine-cosine potentiometer, and a DC voltage proportional to cosine B appears on the cosine output 66 of said potentiometer.

The third sine-cosine potentiometer registrating the angle C is indicated by 67. The reference DC voltages ± E' volt are applid to the fixed terminals of the third sine-cosine potentiometer, whereby a DC voltage proportional to sineC appears on the sine output 68 of the third sine-cosine potentiometer, and a DC voltage proportional to cosineC appears on the cosine output of said potentiometer.

The foruth sine-cosine potentiometer registrating the angle D is indicated by 50, cf. FIG. 2. The reference DC voltages ± E' volt are applied to the fixed terminals of the fourth sine-cosine potentiometer, whereby a DC voltage proportional to sineD appears on the sine output 71 of the fourth sine-cosine potentiometer, and a DC voltage proportional to cosineD appears on the cosine output 72 of said potentiometer.

The summation of the output voltages of the first three sine-cosine potentiometers 61, 64, and 67 may be performed as a matter of course for providing an electrical representation as the point $P_1$ with the coordinates $(x_1, y_1)$, cf. the equations (I) and (II).

It is, however, not so simple as far as the angle D is concerned. A circuit has been provided due to the fact that one revolution of the transducer wheel 23 involves a successive cutting in and out of the four transducers. This circuit causes an automatically 90° shifting backwards of the sweep each time a transducer is cut out and the subsequent one is cut in. Subsequently the sweep follows the transducer cut in in its 90° passage through a circular sector. This sequence of operation is repeated four times at each rotation of the transducer wheel. It appears from FIGS. 3 and 5 that the angle D must pass through the values from −45° to +45° during the rotation of the wheel 23, i.e. that sineD must pass through the values from $-\sqrt{2/2}$ to $+\sqrt{2/2}$, whereas cosineD must pass through the values from $\sqrt{2/2}$ to 1 and back again to the value $\sqrt{2/2}$.

The voltage of a complete rotation of the transducer wheel 23 on the sine output of the fourth sine-cosine potentiometer 50 is indicated by a full-drawn line, cf. FIG. 7. This explains the indication $sineD_0$, since the angle D assumes the values from −45° to +45° only. The inverted curve $-sineD_0$ of the sine curve is indicated by a dotted line. It is to be noted that the curves intersect the abscissa axis of $D_0 = 0°$, 180°, and 360°. This means, of course, that the main axis of one of the transducers is chosen as the zero reference, and that the gear wheels 52 and 53 are engaged in such a manner that the sine and cosine outputs of the potentiometer deliver the voltage 0 and +E' volt respectively, when the main axis of the transducer is identical with the symmetry axis of the transducer head.

The corresponding values of $cosineD_0$ and $-cosineD_0$ are shown in FIG. 8.

The voltages illustrated are provided by means of four operational amplifiers, and the sine output of the sine-cosine potentiometer 50 is connected to the input of a first operational amplifier 73 with the amplification 1 in such a manner that the output 74 of the operational amplifier 73 also delivers a voltage proportional to $sineD_0$.

The operational amplifiers mentioned below serve impedance matching purposes only if nothing else is stated.

The cosine output of the sine-cosine potentiometer is connected to the input of a second operational amplifier 75 with an amplification 1 in such manner that the output 76 of the second operational amplifier 75 also delivers a voltage proportional to $cosineD_0$. The first operational amplifier 73 is connected to the input of a third operational amplifier 77 in an inverting coupling, whereby the output 78 of said third operational amplifier delivers a voltage proportional to $-sineD_0$. The second operational amplifier 75 is connected to a fourth operational amplifier 79 in an inverting coupling in such manner that the output 80 of said fourth operational amplifier delivers a voltage proportional to $-cosineD_0$.

The products stated in the equations (V) and (VI) necessitate however, only fragments of the curves illustrated in FIGS. 7 and 8. The desired function of sineD has a sawtooth like sequence with a zero passage through 0°, 90°, 180°, and 270°. The function values are between $-\sqrt{2/2}$ and $\sqrt{2/2}$ corresponding to the cutting-in of a transducer when $D = -45°$ and to the cutting-out of the transducer when $D = +45°$. The desired function of cosineD comprises four curve tops of the maximum values of $D = 0°$, 90°, 180°, and 270° in the interval between the function values $-\sqrt{2/2}$ and 1.

By comparing FIGS. 7, 8, and 9 it appears that the fragment $cosine_1$ is identical with the curve of $cosineD_0$ in FIG. 8 for $-45° < D_0 < 45°$ in which the transducer 1 is cut in, whereas the fragment $sine_1$ is identical with the curve of $sineD_0$ in FIG. 7. In the next interval $45° < D_0 < 135°$ in which the transducer 2 is cut in the fragment is identical with the curve of $sineD_0$, whereas the fragment $sine_2$ is identical with the curve of $-cosineD_0$, etc.

The choice of the individual fragments is made by means of a comparator and switch circuit generally shown at 81 in FIG. 6 and illustrated in detail in FIG. 10.

FIG. 10 illustrates the four operational amplifiers 73, 75, 77, and 79 providing the four values $sineD_0$, $cosineD_0$, $-sineD_0$, and $-cosineD_0$ respectively.

The comparator circuit comprises four comparators 82-85, which may be operational amplifiers coupled in a special manner. Their + inputs are connected in parallel to the contact arm 87 of a linear potentiometer 86. A reference DC voltage is applied to the fixed terminals of the potentiometer 86, and the contact arm 87 is adjusted in such a manner that a voltage $\sqrt{2/2}$ the reference voltage E' volt of the potentiometer 50 is applied to the + inputs of the comparators.

The output 74 of the first operational amplifier 73 is connected to the input of the first comparator 82 whereas the output 76 of the second operational amplifier 75 is connected to the = input of the second comparator 83. The output 78 of the third operational amplifier 77 is connected to the − input of the third comparator 84 and finally the output 80 of the fourth operational amplifier 79 is connected to the − input of the fourth comparator 85. The outputs of the comparators are connected in parallel via the respective diodes 88 and a common resistor 90 to a DC voltage source E″. The output voltage of the individual comparators is positive when the voltage on the − input is lower than the voltage on the + input. A negatively going change in voltage appears on the output as soon as the voltage on the − input is higher than the voltage on the + input. The output remains in this low voltage level until the voltages on the input change again. This negatively going change in voltage is utilized as a gate pulse for the control of eight analogous gates in the form of field-effect transistors 91-98. These analogous gates are inserted between the operational amplifiers 73, 75, 77, and 79 and a sine output 100 and a cosine output 101 of the comparator circuit 81 in the following manner. The emitter and the collector of the first FET 91 are connected to the output 78 of the third operational amplifier and the sine output 100 of the comparator circuit. The emitter and the collector of the second FET 92 are connected to the output 78 of the operational amplifier and the cosine output 101 of the comparator circuit. The output 74 of the first operational amplifier is connected to the cosine output 101 via a third FET 93 and to the sine output via a fourth FET 94. The output 76 of the second operational amplifier is connected to the cosine output 101 via the fifth FET 95 and to the sine output 100 via the sixth FET 96, and the output 80 of the fourth operational amplifier is connected to the sine output 100 via the seventh FET 97 and to the cosine output 101 via the eighth FET 98.

The output of the first comparator 82 is connected in parallel to the gate terminals on the FETs 93 and 97 for the control of the above analogous gates 91-98. The output of the second comparator 83 is connected in parallel to the gate terminals on the FETs 94 and 95. The output of the third comparator 84 is connected to the gates of the FETs 92 and 95 respectively. The output of the fourth comparator 85 is connected to the gates of the FETs 91 and 98 respectively.

A further advantage of the field-effect transistor is the emitter-collector distance being non-conducting when the voltage on the gate is positive, and conducting when the voltage on the gate is negative or at least less positive.

The above sequence of the voltages on the sine output 100 and the cosine output 101 appears from FIG. 9, and is illustrated in the following example in which the transducer 3 is cut in and the angle $D_0$ registered by the sine-cosine potentiometer 50 passes through the angle interval (135°/225°). This is to be compared with the fact that the main axis 18 of the transducer cut in passes through the angle interval (−45°/45°).

The function values for the curve − $cosineD_0$ are only higher than $\sqrt{2/2}$ in this interval, i.e. a negative voltage appears only on the output of the fourth comparator 85 (the voltage on the − input of the remaining comparators 82, 83, and 84 is lower than $\sqrt{2/2} \cdot E'$). This negative or low voltage level is applied to the gate on the FETs 91 and 98 respectively, and these gates will thus be conducting, i.e. the signal on the output 78 of the third operational amplifier 77 is led through to the sine output 100 and the signal on the output 80 of the fourth operational amplifier 79 is led through to the cosine output 101. The sine output 100 receives the signal − $sineD_0$ which passes the correct values from − $\sqrt{2/2}$ to $\sqrt{2/2}$ in the interval in question. The cosine output 101 receives the signal − $cosineD_0$ which passes the values from $\sqrt{2/2}$ to 1 and back again to $\sqrt{2/2}$.

Four analogous two-input multipliers 102-105 are used for the performing of the products of the trigonometric quantities forming part of the equations (V) and (VI). These multipliers are either complete integrated circuits or integrated circuits demanding an adaption by means of external operational amplifiers and other factor determining components such as resistors. A common feature of all the analogous multipliers used is, however, that the output voltage is proportional to the product of the two input voltages.

The sine output of the third sine-cosine potentiometer 67 is connected to the first input 108 of the first multiplier 102 and to the first input 112 of the third multiplier 104 via an operational amplifier 106 acting as impedance matching. The cosine output of the sine-cosine potentiometer 67 is connected to the first input 110 of the second multiplier 103 and to the first input 114 of the fourth multiplier 105 via a second operational amplifier 107.

The sine output 100 of the comparator circuit 81 is connected to the second input 111 of the second multiplier and to the second input 113 of the third multiplier 104. The cosine output 101 of this comparator circuit is connected to the second input 109 of the first multiplier 102 and to the second input 115 of the fourth multiplier 105.

A voltage proportional to sineC appears on the input 108 of the first multiplier 102, and a voltage proportional to cosineD appears on the input 109 thus causing a voltage proportional to the product sineCcosineD on the output 116.

Voltages proportional to cosineD and sineD respectively appear on the outputs 110 and 111 of the second multiplier 103, and a voltage proportional to the product cosineCsineD consequently appears on the output 117.

Voltages proportional to sineC and sineD respectively appear on the inputs 112 and 113 of the third multiplier 104, and a voltage proportional to the product sineCsineD appears on the output 118. The output 118 of the multiplier is made inverting since this voltage is to be considered negative, cf. the equation (VI).

The inputs 114 and 115 of the fourth multiplier 105 receive voltages proportional to cosineC and cosineD respectively, and a voltage proportional to the product cosineCcosineD appears consequently on the output 119.

The outputs of the first two multipliers are connected to the input of a summation operational amplifier or a first summator 121 the output of which supplies a voltage proportional to the sum sineCcosineD + cosineCsineD or, for short, sine (C + D). The outputs of these two multipliers are connected to the input of a second summator 122 the output of which supplies a voltage proportional to the sum cosineCcosineD − sineCsineD or, for short, cosine (C + D).

The distance $d$ from the point $P_1$ to the reflection point P is represented by a sawtooth voltage generated by two sweep generators 123 and 124 each comprising an operational amplifier 125 and 126 respectively having an external R-C stage. The individual condensator in these R-C stages is shunted by the emmitter-collector distance of a field-effect transistor 127 respectively.

The FETs are non-conducting when a negative voltage level is applied to the gate and conducting when a positive voltage level is applied to the gate. The gate terminals of the two field-effect transistors are connected in parallel to the output 131 of a 400 μ pulse generator 130. The input 132 of the pulse generator 130 connected to the output of an ultrasonic generator (not shown) via a terminal 133. The ultrasonic generator supplies the transducer cut in with short strong pulses via the pulse conductor 60 at a suitable pulse rate, e.g. 1000 pulses per second. The ultrasonic pulse generator is not illustrated since it forms part of a standard component in a standard ultrasonic apparatus. The pulse generator 130 is trigged each time the ultrasonic pulse generator supplies the transducers with a pulse. Subsequently the pulse generator 130 applies a negative pulse to the gate terminals of the FETs 127 and 128 whereby the FETSs become non-conducting. In this way the short circuit of the condensators of the R-C stages is relieved, and the sweep generators or the integrators 125 and 126 generate a sawtooth voltage. The slope of the sawtooth voltage is proportional both to the product of the time constant of the R-C stage in the individual integrator and to the values sine (C + D) and cosine (C + D) respectively of the input, i.e. the voltage on the output of the first sweep generator 123 represents the term $d\sin(C+D)$ in the equation (III), and the output of the second sweep generator 124 represents the term $d\cos(C+D)$ in the equation (IV). The low voltage level on the gate terminals of the FETs changes to a high level when the 400 μ pulse stops whereby the condensators in the R-C stages are short-circuited and the sweep voltages return to the output level.

Furthermore the sawtooth voltage of each individual sweep generator starts on a DC voltage level higher than zero representing the fixed distance $d_0$ between the individual ultrasonic crystal and the axis of rotation of the transducer wheel. Thus the distance $d_0$ represents the radius of the transducer wheel. This means that the sawtooth voltages must start on DC voltage levels corresponding to $d_0\sin(C+D)$ and $d_0\cos(C+D)$ respectively. These DC voltage levels are easily provided by adjustment of the DC voltage delivered by the multipliers. The output voltages of the sweep generators 123 and 124 are finally added to the function voltages of the sine-cosine potentiometers 61, 64 and 67 in a total summation circuit 135. The summation circuit substantially comprises a third summator 136 and a fourth summator 137.

The cosine outputs 63, 66 and 69 of the three first sine-cosine potentiometers and of the first sweep generator 123 are connected in parallel to the input of the third summator 136 via summation resistors generally shown at r. Thus a voltage proportional to $a\cos A + b\cos B + c\cos C + d\sin(C+D)$ appears on the output terminal 138 of the third summator 136. This formula is identical with the electrical representation of the x-coordinate of the point P apart from the reference coordinate $x_0$, cf. the equations (I) and (III). The output terminal 138 of the summator is in a known way connected to the x-deflection amplifier (not shown) of the oscilloscope.

The sine outputs 62, 65, and 68 of the first three sine-cosine potentiometers and the output of the second sweep generator 124 are connected in parallel to the input of the fourth summator 137 via other summation resistors r. Thus a voltage proportional to $a\sin A + b\sin B + c\sin C + d\cos(C+D)$ appears on the output 139 of the fourth summator 137. This formula is identical with the electric representation of the y-coordinate of the point P apart from the reference coordinate $Y_0$, cf. the equations (II) and (IV). The output terminal of the summator is connected in a known way to the y-deflection amplifier (not shown) of the oscilloscope.

The fact that summation resistors are generally shown at r does not mean that they are of equal ohmic value. Resistors are mentioned collectively as it is elementary to a person skilled in the art to dimension these resistors so that the correct sum appears on the output of the summator in question.

A relay contact 140 has been inserted in the signal pulse conductor 60 for safeguarding the reed switches 36 in the transducer wheel against damage when they open and close. This relay contact 140 is controlled by a relay coil 141, which is activated by a control circuit 142. The control circuit 142 receives gate pulses both from a third output 143 in the comparator circuit 81 and from the output 131 of the 400 μ pulse generator 130. These two signals control a blanking circuit 144 the output 145 of which is connected to the z-input of an oscilloscope (not shown). The relay coil 141 cannot receive current until the reed switches are closed and if it receives current it stops receiving said current shortly before the switches open. This sequence is electrically controlled in such a manner that the reference voltage to the comparators 82-85, cf. FIG. 10, is adjusted to a value higher than $\sqrt{2/2}\ E'$ by means of the linear potentiometer 86. In this way the negatively going chain in voltage on the output of one of the comparators will appear later on, i.e., when the angle D is larger than $-45°$ (i.e. numerically less than 45°). The negative change in voltage also appears on the third output 143 of the comparator circuit 81, and it is conducted to the control circuit. The control circuit then closes the relay contact 140 and thereby connects the transducer already cut in at one of the reed switches to the ultrasonic pulse generator. In the same manner the low voltage level stops on the output of one of the comparators shortly before the angle D assumes the value 45° making the relay contact 140 open. The relay contact 140 opens the connection between the activated transducer and the ultrasonic generator before the above reed switch opens. In this way the circuit sector, in which the transducer scans, becomes less than 90°.

The blanking circuit 144 is controlled by the square pulse from the pulse generator 130 and and switches off the electronic beam of the oscilloscope during the shifting backwards of said electronic beam 144 furthermore switches off the square pulse from the comparator circuit 81. Thus the electronic beam is switched off during the shifting of the transducer and of the angle thus preventing disturbing signals from appearing on the oscilloscope screen during these operations.

The above detailed description is, of course, only meant as an illustrative example of an embodiment of the invention. The transducer described is used together with a split scanning arm, it may, however, be used together with any known arrangement moving the transducer in the sectional plane. It comes within the sphere of the person skilled in the art to adapt the original position determining circuits to the electronical circuits attached to the change of transducer and angle.

It is, for instance, also possible within the scope of the invention to drive the transducer wheel directly by means of a motor built into the transducer housing and thus rendering the Bowden cable superfluous.

We claim:

1. An apparatus for recording an ultrasonic sectional view comprising a transducer head (20) with a pulse circuit for transmission and reception of ultrasonic energy, means for visualizing received reflected ultrasonic signals on a cathode-ray tube, and a scanning arm (17) for moving the transducer head in a sectional plane along a plane curve corresponding to the outline (11) of the body (10) examined in the sectional plane, said apparatus comprising data potentiometers and analogous calculating circuits for producing electrical signals representing the positions of the reflection points (P) of the ultrasonic echoes in a rectangular XY-system of coordinates in the sectional plane, characterized by the transducer head (20) comprising four ultrasonic transducers (33) built into the periphery of a transducer wheel (23) at equidistant angular distance for bound rotation about an axis (26) perpendicular to the sectional plane, said transducer wheel (23) comprising means for separately and successively cutting the transducers (33) in and out of the pulse circuit in such manner that each transducer covers only a sector (angle D) from $-45°$ to $+45°$ about a symmetry axis (49) for the transducer head (20), the transducer head comprising a sine-cosine potentiometer (50) mechanically coupled to the transducer wheel (23) for the registration of the angle (D), and by the apparatus comprising means for resetting the angle (D) 90°, said angle being registered by the sine-cosine potentiometer at each changing over from one transducer (33) to the subsequent one.

2. An apparatus as claimed in claim 1, characterized by an asynchronous motor with an infinitely variable gear indirectly driving the transducer wheel (23) through a Bowden cable (31) and a chain drive (28, 29, 30).

3. An apparatus as claimed in claim 1, characterized by the means for separately and successively cutting the transducers (33) in and out of the pulse circuit comprising four reed switches (36) built into the transducer wheel (23), one side of said reed switches being connected to a transducer and the opposite side being connected in parallel via a slip ring (40) on the axis (27) of the transducer wheel to a common conductor (38) secured to said axis (27) of the transducer wheel, on which slip ring a slip contact (42) slipping, said slip contact being connected to the pulse circuit by means of the inner conductor (44) of a coaxial cable (43); and a fixed permanent magnet (37) for activating the reed switches (36) separately and a relay contact (140) inserted in the pulse circuit (60) and controlled by a control circuit (142), said relay contact only connecting the individual transducer (33) to the pulse circuit (via 133) when the associated reed switches (36) have been opened and closed respectively.

4. An apparatus as claimed in claim 1, characterized by the means for resetting the angle (D) 90°, said angle being registered by the sine-cosine potentiometer (50) at each changing over from one transducer to the subsequent one comprising a plurality of operational amplifiers (73, 75, 77, 79) providing the functions sineD, cosineD, $-$ sineD, and $-$ cosineD, and a plurality of comparators (82-85) coupled to their respective operational amplifier and to a reference DC source (86), and by the outputs of the comparators controlling a plurality of analogous gates (91-98) for providing a sine voltage on a sine output (100) varying from $-\sqrt{2}/2$ to $\sqrt{2}/2$ and a cosine voltage on a cosine output (101) varying from $-\sqrt{2}/2$ to 1 and back to $-\sqrt{2}/2$ from the moment when a transducer is cut in and till the moment when said transducer is cut out.

* * * * *